United States Patent [19]

Gould et al.

[11] Patent Number: 5,334,691

[45] Date of Patent: * Aug. 2, 1994

[54] HYDROPHILIC POLYURETHANES OF IMPROVED STRENGTH

[75] Inventors: Francis E. Gould, Princeton; Christian W. Johnston, Neshanic Station, both of N.J.

[73] Assignee: Tyndale Plains-Hunter Ltd., Princeton, N.J.

[ * ] Notice: The portion of the term of this patent subsequent to Jun. 9, 2009 has been disclaimed.

[21] Appl. No.: 872,893

[22] Filed: Apr. 23, 1992

Related U.S. Application Data

[62] Division of Ser. No. 561,240, Jul. 24, 1990, Pat. No. 5,120,816.

[51] Int. Cl.$^5$ .......................... C08G 18/30; A61F 2/14
[52] U.S. Cl. ........................ 528/76; 424/409; 424/484; 424/486; 424/501; 604/372; 604/228; 623/5; 623/7; 623/12; 521/176; 521/159
[58] Field of Search .................... 528/76, 65; 521/159, 521/176; 424/409, 486, 501

[56] References Cited

U.S. PATENT DOCUMENTS

| | | | |
|---|---|---|---|
| Re. 32,834 | 1/1989 | Cordts et al. | 523/114 |
| 2,977,330 | 3/1961 | Brower | 521/159 |
| 3,503,933 | 3/1970 | Kaizerman et al. | 526/64 |
| 3,539,482 | 11/1970 | Stewart | 528/76 |
| 3,793,241 | 2/1974 | Kyle et al. | 524/905 |
| 3,822,238 | 7/1974 | Blair et al. | 260/75 |
| 3,925,319 | 12/1975 | Hiatt et al. | 260/75 |
| 3,975,350 | 8/1976 | Hudgin et al. | 260/75 |
| 4,068,035 | 1/1978 | Violpand et al. | 428/279 |
| 4,083,831 | 4/1978 | Santosusso | 260/75 |
| 4,153,777 | 5/1979 | Stagel | 528/60 |
| 4,156,066 | 5/1979 | Gould | 528/73 |
| 4,156,067 | 5/1979 | Gould | 528/73 |
| 4,235,988 | 11/1980 | Fildes et al. | 528/79 |
| 4,355,119 | 10/1982 | Pechhold | 521/159 |
| 4,359,558 | 11/1982 | Gould et al. . | |
| 4,367,327 | 1/1983 | Holker et al. | 528/61 |
| 4,385,133 | 5/1983 | Alberino et al. | 521/159 |
| 4,447,590 | 5/1984 | Szycher | 528/76 |
| 4,451,635 | 5/1984 | Gould et al. | 528/71 |
| 4,454,309 | 6/1984 | Gould et al. | 525/454 |
| 4,463,156 | 7/1984 | McGary, Jr. et al. | 528/65 |
| 4,496,535 | 1/1985 | Gould et al. | 428/343 |
| 4,517,326 | 5/1985 | Cordts et al. | 524/310 |
| 4,743,673 | 5/1988 | Johnston et al. | 528/60 |
| 4,789,720 | 12/1988 | Teffenhart | 528/76 |
| 4,810,543 | 3/1989 | Gould et al. | 528/76 |
| 5,000,955 | 3/1991 | Gould et al. | 424/409 |
| 5,120,816 | 6/1992 | Gould et al. | 528/76 |

FOREIGN PATENT DOCUMENTS 8905319 6/1989 PCT Int'l Appl. .................. 528/76

OTHER PUBLICATIONS

Walder, A. J. et al., "Thermoplastic Polyurethaneureas Synthesized with Water as an Extender", The 17th Annual Meeting of the Society for Biomaterials, May 1–5, 1991.

Primary Examiner—Paul R. Michl
Assistant Examiner—Peter F. Kulkosky
Attorney, Agent, or Firm—Mathews, Woodbridge & Collins

[57] ABSTRACT

The strength and integrity of hydrophilic polyurethane resins prepared by reacting a diol component, an organic chain extender and an organic diisocyanate are improved by critical selection of the diol component, the amount of water in the reaction mixture and the mole ratios of the reactants. The diol component is at least one of (1) a long chain poly(oxyethylene) glycol of molecular weight above 2500 and (2) a medium chain poly(oxyethylene) glycol or polyester glycol of 250–2500 molecular weight. The chain extender is a difunctional compound having a molecular weight of less than 250. The amount of water in the reaction mixture is 0.5 to 2.5 weight % and the urea content of the resins is from about 13.6 to 33.7 weight %. This invention also includes uses of these hydrophilic polyurethane resins as carrier vehicles for various active agents including a medicament, fungicide, pesticide, insecticide, fertilizer, fragrance, flavor, sun-screen, depilatory, cosmetic, contraceptive, anti-fogging agent, hair spray formulation and perfume.

8 Claims, 6 Drawing Sheets

WATER CONTENT OF HYDRATED POLYMERS
vs.
PERCENT OF UREA MODIFICATION

SOLID LINE - DRY POLYMER
DASHED LINE - HYDRATED POLYMER

TEAR RESISTANCE
vs.
PERCENT OF UREA MODIFICATION

SOLID LINE - DRY POLYMER
DASHED LINE - HYDRATED POLYMER

Fig. 2

TEAR RESISTANCE vs. PERCENT OF UREA MODIFICATION

SOLID LINE = DRY POLYMER
DASHED LINE = HYDRATED POLYMER

Fig. 3

TENSILE STRENGTH OF HYDRATED POLYMERS
vs.
PERCENT OF UREA MODIFICATION

HYDROPHILIC POLYURETHANES OF IMPROVED STRENGTH

This application is a division of application Ser. No. 07/561,240, filed Jul. 24, 1990, now U.S. Pat. No. 5,120,816.

TECHNICAL FIELD

This invention relates to hydrophilic polyurethane resins modified during the preparation thereof to provide improved strength.

BACKGROUND OF THE INVENTION

Hydrophilic polyurethane resins are prized because of their ability to absorb large amounts of water and to form stable, water-insoluble hydrogels. In the water-swelled state, hydrophilic polyurethanes vary from gel-like to soft and pliable character and the dry state from soft to hard and machinable quality. The degree of hydrophilicity is a function of the type and proportion of polar groups in the backbone of the polymer, which groups are controlled by appropriate selection of the reactive hydrogen terminated resins or compounds used in the polymer synthesis. These reactive resins and compounds include a variety of polyamines, diols and polyols (polyether or polyester), hydroxyl-containing polycarboxylic acids, and blends of such resins and compounds as well as resins and compounds having mixed functionality. Typical hydrophilic polyurethanes are described in U.S. Pat. Nos. 3,822,238 and 3,975,350. Later patents (such as U.S. Pat. Nos. 4,359,558 and 4,451,635) describe improved versions of the polymers, including polymer s based on hydroxyl substituted lactones. The lactone groups and the excess hydroxyl free carboxylic acid groups and the excess hydroxyl groups permit cross-linking of the polyurethanes (U.S. Pat. Nos. 4,156,066 and 4,156,067).

Hydrophilic polurethanes have a host of uses including catheters and other tubing, low wet-friction coatings, denture liners, cannulae, body implants including corneal prosthesis, contact lenses, dialysis membranes, absorbents, controlled release devices and carriers for drugs and other agents, condoms, swellable fabrics, gauzes, films such as surgical drapes, diaper linings, solubilizing packaging components, water-transmitting coated fabrics, water-swelling caulks, artificial leather, gas filters, oil-resistant shapes, and personal care products, such as hair sprays, nail polishes and the like.

In certain of the foregoing and other applications, increased strength of the polyurethane, including dimensional stability, can be a significant factor. For example, hydrophilic polyurethanes can be used in the manufacture of intravenous catheter tubing because of blood and body fluid compatability, and the ease with which such tubing can be introduced through a needle into a vein. The softening and ease of passage of the tubing of the polyurethane upon hydration (resulting from contact with body fluids) increases the comfort and ease of passage of the tubing. The inside diameter of the tubing also expands upon the hydration, thereby increasing the volumetric flow rate of a fluid being administered through the tubing. Nevertheless, although the tubing can be made sufficiently thin to pass through a needle, the stiffness of the tubing extruded from conventional hydrophilic polyurethanes is insufficient for insertion into veins and other body channels without the needle. It is evident, therefore, that if a hydrophilic polyurethane resin can be modified during processing in such a way that tubing formed of the resin will not only hydrate and thereby swell and soften upon contact with body fluids but will also have sufficient stiffness before such contact, the tubing can be inserted into and moved easily through a vein or other body channel without a needle. This will avoid the discomfort of needles and prevent the tubing from folding back upon itself. The use of stiffened tubing in place of needles also eliminates the risk of contamination sometimes accompanying the use of needles, e.g., transmission of the AIDS virus.

Improved strength, manifested by increased stiffness and integrity, has significance also for many other applications of the hydrophilic polyurethanes, particularly when used as carriers in the animal body and other environments for release of active agents such as medicaments. For example, when used as carriers, increased strength enables the polyurethanes to transport a medicament or other agent through body channels more effectively because the polyurethane will not soften and disintegrate as quickly upon contact with body fluids as will conventional hydrophilic polyurethanes. Accordingly, hydrophilic polyurethanes which combine the softening and limited swelling resulting from hydrophilic character with strength and integrity sufficient to enable tubing or other products constructed of the polyurethane to travel more effectively in a closed environment or to support greater loads, will have greater usefulness.

It is well known that water in a polyurethane precursor formulation can cause foaming during the polymerization, and that water in a hydrophobic polyurethane precursor formulation can assist in producing foams ranging from flexible to rigid. Nevertheless, so far as is known there have been no studies on controlling the amount of water relative to the character and amount of diol and NCO/OH ratio in a hydrophilic polyurethane formulation in order to provide a suitable balance of water absorbency, softness and strength in the resulting polymer.

Typical of the technical literature and patents describing the use of water in preparing polyurethane foams is J. H. Saunders et al., Polyurethanes: Chemistry and Technology, Part I, Interscience Publishers, New York (1962)on hydrophobic polyurethanes, and U.S. Pat. Nos. 4,359,558, 4,454,309, 4,454,535, 4,451,635, 3,793,241, 4,083,831, 4,517,326, 2,977,330 and 4,153,777. In the foregoing patents, water is present in the reaction mixture either as a result of the hygroscopic nature of a glycol reactant or as the result of intentionally adding water to the reaction mixture to induce foaming. None of the patents, however, describe the relationships determined in the present invention as controlling the strength of a product hydrophilic polyurethane.

SUMMARY OF THE INVENTION

It has now been found that by carefully selecting the diol component of a hydrophilic polyurethane and critically controlling the amount of water in the reaction mixture, the polyurethane can be modified to improve its strength sufficiently for enhanced utility but without unduly reducing hydrophilic character. The improved strength is reflected in greater hardness and stiffness but without substantial diminution of other desirable properties and without rendering the product so brittle that it shatters or otherwise disintegrates prematurely. The balance of hydrophilicity, softness and strength in the hydrophilic polyurethanes of the invention is an outstanding and surprising achievement in view of the paucity of published information on hydrophilic polyurethanes.

According to one aspect of the invention, a substantially non-covalently crosslinked hydrophilic polyurethane having improved strength is produced by reacting: (A) a diol component selected from at least one of (1) a long chain poly(oxyethylene) glycol having a number average molecular weight above 2500, and (2) a medium chain poly(oxyalkylene) glycol or polyester glycol, having a number average molecular weight of from 250 to 2500; (B) at least one organic chain extender having a molecular weight of less than 250; (C) water; and (D) an organic diisocyanate; wherein the mole ratios of the diol component A and water per tool e of chain extender B are (i) 0.4 to 0.5 of diol component (1) and 1.5 to 8.0 of water;

(ii) 0.1 to 0.75 of diol component (2) and 0.05 to 3.3 of water; and (iii) 0.06 to 0.04 of diol component (1), 0.1 to 0.2 of diol component (2) and 0.25 to 1.25 of water.

wherein the NCO:OH ratio is in the range of 0.85:1 to 1.1:1, preferably 0.9:1 to 0.98:1, and the amount of water in the reaction mixture is in the range of 0.5 to 2.5 wt. % based on weight of total formulation exclusive of catalyst, preferably about 0.7 to 2.0 wt. %.

In other aspects of the invention, articles of manufacture are provided comprising shaped bodies formed of the hydrophilic polyurethane described above, typically in the form of a film such as surgical drapes, gloves or condoms; a tubular member such as cannulae having walls formed of the hydrophilic polyurethane; a body implant containing a medicament; or a delivery system comprising an active agent (such as a medicament) and the hydrophilic polyurethane as a carrier for the active agent. In still another aspect of the invention, the hydrophilic polyurethane comprises a coating useful on various substrates including boat hulls and the interior walls of a conduit for transporting aqueous fluids in industrial environments.

DETAILED DESCRIPTION

As indicated above, the hydrophilic polyurethanes of the invention are substantially noncovalently crosslinked reaction products of (A) a diol component, (B) an organic chain extender, (C) water and (D) an organic diisocyanate. The diol component (A) is selected from at least one of (1) a long chain poly(oxyethylene) glycol having a number average molecular weight above 2500, typically about 3000–12000, preferably about 5000–9000, and (2) a medium chain poly(oxyalkylene)-glycol or polyester glycol, having a number average molecular weight of from 250 to 2500, preferably about 500–2000. Suitable long and medium chain poly(oxyethylene) glycols are available commercially from several sources, such as the water soluble "Carbowax" products sold by Union Carbide Corporation. In contrast, the polyester glycols are more hydrophobic and are particularly useful when a biodegradable product is required. However, because of biodegradability, hydrophilic polyurethanes based on polyester glycols cannot be used in the body. Preferably, all or a major amount (more than 50 wt. %) of the diol component will be a poly(oxyethylene) glycol.

The medium chain polyester glycols are well known products derived from the condensation of one or more alkylene glycols with one or more dibasic acids and include, for example, reaction products of x moles of a difunctional acid such as adipic, sebacic, dimeric acid, phthalic and maleic acid and x+1 moles of difunctional linear glycols such as ethylene glycol, polyethylene glycols (number average molecular weight about 100–600, preferably 200–300), propylene glycol, polypropylene glycols (number average molecular weight 100–600, preferably 200–300), 1,4 butane diol, polybutylene glycols, and the like. Mixtures of acids and/or glycols may be used and the value of x may vary from 1 to about 10, lower values of x being preferred for use with higher molecular weight glycols. The molecular weight of the polyester glycol increases as x increases, the preferred value of x being 3–6. However, the molecular weight should not be so high that the ester portion becomes the major portion of the polymer, an undesirable result due to the hydrophobic character of ester groups. Preferably, the number average molecular weight of the polyester glycol, if present, should not be over 1000.

The medium chain poly(oxyalkylene) glycols are derived from $C_2$-$C_4$ alkylene oxides such as oxyethylene, oxypropylene, oxybutylene and oxytetramethylene (such as the blend of linear polytetramethylene ether glycols sold by DuPont under the brand "Terathane"), and further include block copolymer polyols obtained by adding ethylene oxide to a polyoxypropylene chain. When the sole diol component is a medium chain poly (oxyalkylene) glycol, the diol component should predominate (at least 50 wt. %) in a poly (oxyethylene) glycol. In all formulations of the invention, at least 10–15% by weight of the formulation (exclusive of catalyst) should be a long or medium chain poly (oxyethylene) glycol in order to obtain sufficient hydrophilicity in the polyurethane product.

The reaction mixture also includes one or more organic chain extending compounds (B) having a molecular weight of less than 250, preferably about 150–200, selected from difunctional (active hydrogen containing) straight or branched chain aliphatic compounds, cyclic compounds and aromatic compounds, and any mixtures thereof, in which the functional groups are of substantially equal reactivity. Examples include diols such as ethylene glycol, diethylene glycol, triethylene glycol, 1,4-butanediol, hexamethylene glycol, thiodiglycol, 2,2-dimethyl propane-1,3-diol, 1,4-bishydroxymethylbenzene, bishydroxyethyl disulphide, cyclohexanedimethanol and hydroquinone; diamines such as ethylene diamine hexamethylene dieunine and 1,4- butylene dieunine; dihydrazides such as carbodithydrazide, oxalic hydrazide, hydrazine and substituted hydrazines. The preferred chain extenders are ethylene glycol, diethylene glycol and other alkylene glycols of 2 to 6 carbon atoms.

In selecting the diol component and organic chain extender, care should be taken to avoid polyfunctional compounds which will cause substantial covalent crosslinking of the polyurethane product. However, physical crosslinking in the sense of reversible or reformable crystallite networks resulting from Vander Waals or other physical bonding forces is permissable. Substantial amounts of covalent crosslinking will unduly reduce the hydrophilic character of the product and render the product insoluble in solvent, or difficult or impossible to tool d, extrude or melt process.

The organic diisocyanate reactant (D) is any aliphatic, alicyclic, aliphatic-alicyclic, aromatic or aliphatic-aromatic compound of from 4 to 26 carbon atoms, more usually from 6 to 20 carbon atoms and preferably about 8–15 carbon atoms. Representative isocyanates are: tetramethylene diisocyanate, hexamethylene diisocyanate, trimethylhexamethylene diisocyanate, dimer acid diisocyanate, isophorone diisocyanate, diethylbenzene diisocyanate, decamethylene 1,10-diisocyanate, cyclohexylene 1,2-diisocyanate, cyclohexylene 1,4-diisocyanate and methylenebis(cyclohexyl-4-isocyanate); and the aromatic isocyanates such as 2-4- and 2,6-tolylene diisocyanate, 4,4-diphenylmethane diisocyanate, 1,5-naphthalene diisocyanate, dianisidine diisocyanate, tolidine diisocyanate, xylylene diisocyanate, and tetrahydronapthalene-1,5 diisocyanate.

The preferred isocyanate is methylene bis(cyclohexyl-4-isocyanate) sold by Mobay Chemical Corp. under the trademark "DESMODUR W." Other preferred isocyanates are trimethyl hexamethylene diisocyanate and isophorone diisocyanate. Organic isocyanate equivalents which produce urethane linkages may also be used, including the nitrile carbonates such as adiponitrile carbonate.

Crucial to the success of the invention is control of the mole ratios of the reactants, the amount of water incorporated in the reaction mixture, and the NCO/OH ratio. These variables are interrelated and affect the balance of properties required for effective use of the polymers, particularly the relationship between hydrophilicity and strength. It has been found experimentally, for example, that the amount of water absorbed by the polyurethane and the linear expansion of the polyurethane upon hydration both decrease with the increased urea content of the polymer resulting from reaction of the water with isocyanate groups. At the same time, the properties which reflect improved polymer strength, such as hardness, tensile strength, tensile secant modulus, and tear strength for both dry and hydrated polymer samples, increase with increased urea content. The extent of the changes in hydrophilicity and strength is greater in the case of polymers having low values of the foregoing properties before modification of the urea content of the polymers.

It is known that water will react with isocyanate in a reaction mixture containing polyurethane precursor reactants to form an N-substituted carbamic acid and that under the usual conditions the carbamic acid rapidly decomposes to carbon dioxide and an amine which then immediately reacts with another isocyanate to form a symmetrically disubstituted urea. However, the foregoing reaction heretofore has been used to generate large volumes of carbon dioxide to induce foaming in the reaction mixture and it has not been appreciated that by suitable control of the amount of water relative to selection of the diols (including molecular weights), tool e ratios of reactants and NCO/OH, a balance can be struck between hydrophilicity and the strength afforded by urea linkages such that the resulting polymer will retain a useful degree of hydrophilicity while also exhibiting improved strength. This balance of properties is not due merely to reduction of the amount of hydrophilic components by adding an inert non-water absorbing material such as urea, because it was found that the amount of water absorbed at a 50% increase in urea content was not decreased by half but rather was far less than half. Accordingly, the effect does not result from simple dilution with a urea byproduct but rather from a complex structural modification involving the bonding of water by the hydrophilic diols used in preparing the polyurethane.

Similar considerations apply with respect to the swelling of a polyurethane occurring upon complete hydration: the relationship is more than linear for those polymers showing high levels of swelling. Even in the case of polymers showing a linear relationship between increased urea content and reduction of hydrophilicity, reduction in elongation is greater than the percent of urea in the polymer. As shown in the appended tables and graphs, the improved strength is demonstrated by increase in resin hardness as measured by a Shore D or A penetrometer.

The improved strength resulting from urea linkages introduced by water is a surprising discovery not only for the reasons stated above but also because heretofore it was believed that dimensional stability of a hydrophilic polyurethane resulted from the proportion of short chain glycol, e.g., ethylene or diethylene glycol, in a reaction mixture for forming the polyurethane. It has now been found that the urea content is equally, if not more, important.

The polyurethanes of the invention may be prepared in any manner conventional in the art such as by first forming a homogeneous mixture of the diol component and water, and then reacting the diisocyanate and chain extender with the mixture, or by first forming a prepolymer by reaction of the diisocyanate and one of the diol components, or a portion thereof, followed by reaction with the balance of the diol component, the water and the chain extender. In all cases, the urethane-forming reaction is preferably catalyzed by a known catalyst for the reaction. Suitable catalysts are tin salts and organo tin esters such as stannous octoate and dibutyl tin dilaurate, tertiary amines such as triethylene dieunine (Dabco ®), N,N,N',N'-tetramethyl-1,3-butane diamine and other recognized catalysts for urethane reactions, with care being taken not to heat the reaction mixture unduly since undesirable covalent crosslinking may result. The catalyst is used in amounts effective for catalytic action, e.g., about 0.01 to 1.0 wt. % of the total weight of the reactive components. Reaction temperature should be controlled to avoid excessive foaming. Typically, a useful temperature range is about 50° C. to 90° C. Other reagents may be added to the reaction mixture, as desired, to improve reactive contact or to control viscosity, such as water miscible solvents, suspending agents, and the like.

The invention is further illustrated by the following non-limiting examples of preferred embodiments. In this specification and in the claims, all parts and percentages are by weight and all degrees are centigrade unless otherwise specified.

Preparation of Polyether Polyurethane Resins

Tables 1, 2 and 3 below summarize the reactant formulations and properties of hydrophilic polyurethane polymers prepared from the formulations in a study of the influence of diol component (type and molecular weight) and water on the urea content and strength of the resins. Essentially the same procedure was employed for the synthesis of all of the polymers.

In preparing the resins, the diol components are dried and kept as dry as possible. Those diols that are known to be strongly hygroscopic (such as diethylene glycol) are heated to 80°-85° C. and placed in a vacuum chamber under an absolute pressure of 0.5 mm of mercury or less. When the material stops bubbling it is considered dry, and its water content is analyzed by the Karl-Fischer method.

The diethylene glycol and the other diols ("Carbowax" glycols) to be used in the formulations are mixed in a vessel and reel ted. The temperature is brought to 80° C. and the material again subjected to a vacuum for several hours while maintaining the temperature. This eliminates water in the diols and removes any water picked up in handling and weighing.

The amount of water desired in a formulation is then added to the diol component and after slight mixing the diol component is protected from atmospheric water by covering until cooled to about 70° C. At this point an organic diisocyanate (such as Desmodur W) is added and the mixture stirred. The temperature then drops to near 55° C. When it falls to 53°-55° C. the catalyst is added and active stirring initiated.

After the catalyst is added there is usually a short period of time (generally less than one minute) during which the temperature remains constant. The temperature then begins to rise, slowly at first but with acceleration as time passes. The mixture, originally turbid, becomes clear between 55°-60° C. and the exotherm increases. If water is present the mixture begins to form bubbles at about 80° C. When the temperature reaches 90° C. a foam layer develops. At this point the mixture is poured into a polyethylene container tub and placed in an oven at 100° C. After one to two hours the material is removed and allowed to cool.

The following table summarizes ranges of mole ratios of reactants for preparing preferred polyurethanes of the invention in the manner described above. Other reactants and molecular weights may be employed in accordance with the invention as claimed.

The resin types (A to E) correspond to those of Tables 1-3.

Polyurethane Resins:
Ranges of Moles of Diol Component and Water per Mole Diethylene Glycol

| | Type C | Type B | Type A | Type D | Type E |
|---|---|---|---|---|---|
| PEG$^{(1)}$ | | | | 0.06 –0.07 | 0.40 –0.50 |
| PEG$^{(2)}$ | 0.1 –0.25 | 0.25 –0.50 | 0.50 –0.75 | 0.10 –0.20 | |
| Water | 0.05 –0.72 | 0.25 –1.00 | 0.30 –3.30 | 0.25 –1.25 | 1.50 –10.0 |
| Di-NCO$^{(3)}$ | q.s. to produce NCO/OH = 0.98 | | | | |

$^{(1)}$Carbowax ® 8000 (Union Carbide Corp.) - Polyethylene Glycol, 8000 molecular weight (number average).
$^{(2)}$Carbowax ® 1450 (Union Carbide Corp.) - Polyethylene Glycol, 1450 molecular weight (number average).
$^{(3)}$Desmodur ® W (Mobay Chem. Corp.) diisocyanate Polyurethane Resin Properties In Tables 1, 2 and 3, formulations $A_O$, $B_O$, $C_O$, $D_O$ and $E_O$ contain no water, and formulations A through E of Table 3 are included as representative of conventional hydrophilic polyurethane resins. The latter resins (as well as the Type A to Type E resins outside the scope of the invention) either contain too little or too much water and also differ in the ratios of long chain and medium chain polyethylene glycol to difunctional chain extender (diethylene glycol). The Tables and the appended Graphs show the effects of the water contents and glycol ratios on properties of the resins, reflecting strength in both the dry and wet (hydrated swollen) states.

In the Tables and Graphs, the urea content was calculated from:

$$\text{wt. \% urea} = \frac{13.21W}{(1 - 0.0244W)}$$

where W is the weight of water in a formulation based on Desmodur W diisocyanate. The formula includes a correction for product resin weight decrease due to loss of carbon dioxide produced by the reaction.

The test procedures for determination of properties are as follows:
Hydration (% water content):
Hardness:
  Shore D—ASTM D-22 40-84
  Shore A—ASTM D-2240-84
Tensile Strength: ASTM D-412-83
Tensile 100% Secant Modulas: ASTM D-412-83
Tensile Elongation: ASTM D-412-83
Tear Strength: ASTM D-1004-66

In the graphs of FIGS. 1 to 6, the data point symbols refer to properties of the resins of Tables 1-3 as follows:
Upright triangles:; A-type resins
Downward triangles: B-type resins
Squares: C-type resins
Hexagons: D-type resins
Circles: E-type resins
Points: Conventional resins A and E.

The following conversion chart facilitates comparison of prior art resins with those of this invention.

The table shows, for each of the disclosed resins, the millimoles of polyglycol component, diethylene glycol and water, and the mole ratios of polyglycol to diethylene glycol and water to diethylene glycol. Resin D has two entries under the PEG and PEG:DEG columns (the second entry in parentheses) since D resins comprise both diol components (1) and (2).

These number are readily calculated from the weight percents using a molecular weight of 8000 for diol component (1), 1450 for diol component (2), 106 for diethylene glycol, and 18 for water. The polydiol molecular weights are shown as above.

| MOLAR CONVERSION CHART FOR RESINS | | | | | |
|---|---|---|---|---|---|
| RESIN | PEG | DEG | H2O | PEG:DEG | H2O:DEG |
| $A_0$ | 44 mm | 66 mm | 0 mm | 0.67 | 0.0 |
| A | 42 | 63 | 17 | 0.67 | 0.3 |
| *$A_1$ | 37 | 55 | 60 | 0.67 | 1.1 |
| *$A_2$ | 28 | 42 | 133 | 0.67 | 3.2 |
| $A_3$ | 16 | 24 | 226 | 0.67 | 9.4 |
| $B_0$ | 40 | 87 | 0 | 0.46 | 0.0 |
| B | 38 | 83 | 17 | 0.46 | 0.2 |
| *$B_1$ | 32 | 71 | 67 | 0.45 | 0.9 |
| $B_3$ | 24 | 52 | 145 | 0.46 | 2.8 |
| $B_4$ | 13 | 29 | 238 | 0.45 | 8.2 |
| $C_0$ | 19 | 184 | 0 | 0.10 | 0.0 |
| C | 19 | 180 | 6 | 0.11 | 0.03 |
| *$C_1$ | 14 | 134 | 96 | 0.10 | 0.7 |
| $C_2$ | 9 | 88 | 187 | 0.10 | 2.1 |
| $C_3$ | 5 | 44 | 272 | 0.11 | 6.2 |
| $E_0$ | 11 | 23 | 0 | 0.48 | 0.0 |
| $E_1$ | 10 | 22 | 8 | 0.45 | 0.4 |
| E | 10 | 22 | 28 | 0.45 | 1.3 |

-continued
MOLAR CONVERSION CHART FOR RESINS

| RESIN | PEG | DEG | H2O | PEG:DEG | H2O:DEG |
|---|---|---|---|---|---|
| *$E_2$ | 9 | 20 | 56 | 0.45 | 2.8 |
| *$E_3$ | 7 | 15 | 136 | 0.47 | 9.1 |
| $D_0$ | 6(12) | 90 | 0 | 0.07(.13) | 0.0 |
| D | 5(12) | 86 | 17 | 0.06(.14) | 0.2 |
| *$D_1$ | 5(10) | 75 | 59 | 0.06(.13) | 0.8 |
| $D_2$ | 4(8) | 57 | 131 | 0.07(.14) | 2.3 |
| $D_3$ | 2(5) | 34 | 224 | 0.06(.09) | 6.6 |

The resins of this invention are indicated with an asterisk. Generally the tear strength is many times that of the prior art resins; in some cases ($A_1$, $C_1$, $D_1$, $E_3$), the wet tear strength of the new resins exceeds the dry tear strength of the prior art resins.

Circles: E-type resins
Points: Conventional resins A to E.

The following observations are pertinent to the Tables and Graphs:

(1) Increasing the urea content reduces the expansion of the resins upon complete hydration (see Tables 1-3). The relationship is linear for those resins showing high levels of expansion. Even in the case of resins having a linear relationship of expansion to urea content (see FIG. 1), the reduction in elongation is greater than the percent of urea in the resin.

(2) Modification with urea increases resin hardness as measured by the Shore D penetrometer. The increase is greatest for those resins which initially had low readings (see FIG. 4). Resins with high values at hydration required hardness measurements with a Shore A penetrometer because of softness of the samples (see FIG. 5).

Figure 1:
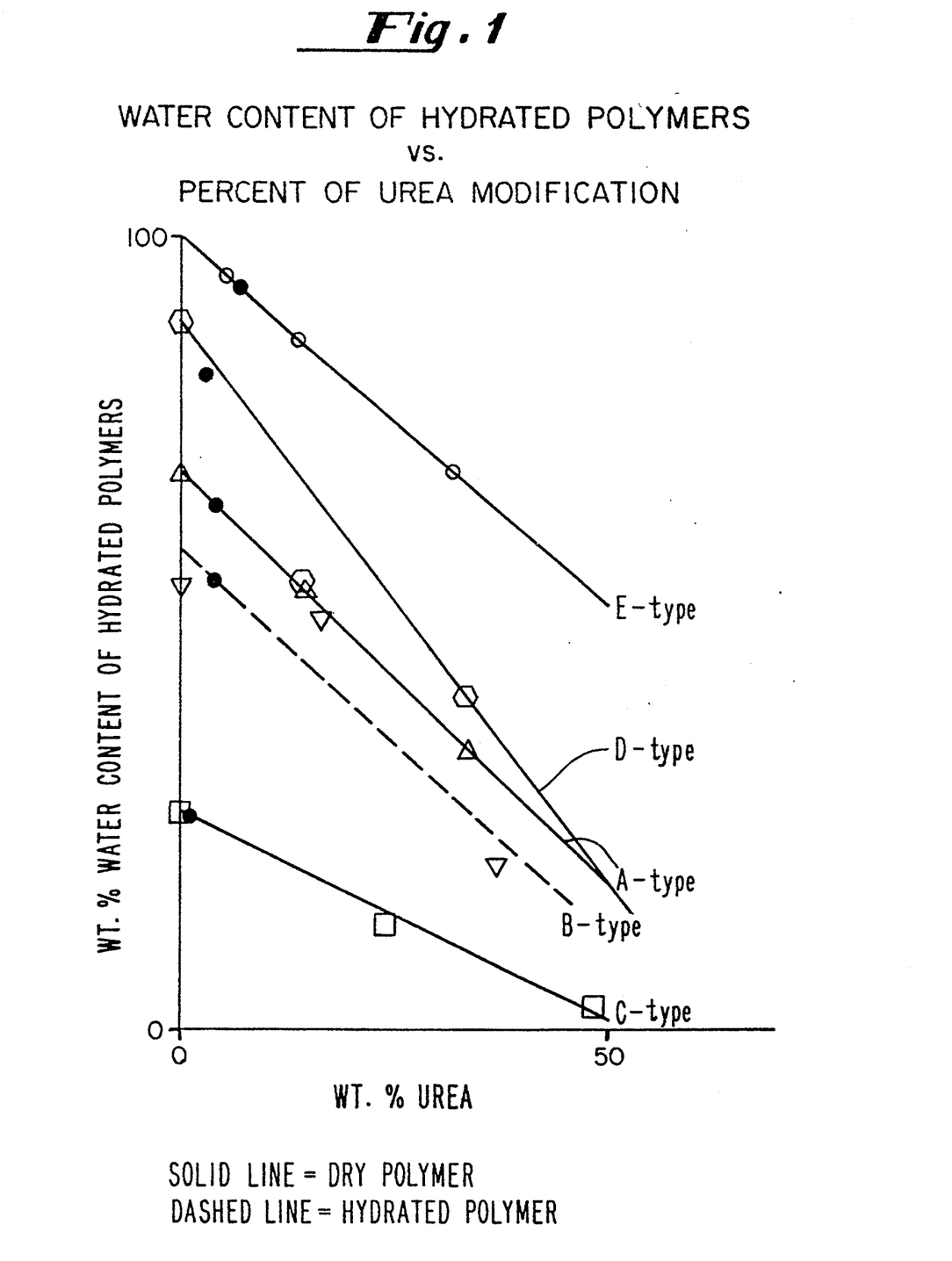
FIGS. 1 to 6 are graphs illustrating some properties of resins of the invention as compared with resins not incorporating water during preparation (resin types $A_0$, $B_0$, $C_0$, $D_0$ and $E_0$ of Tables 1–3 appended) and conventional hydrophilic resins prepared with non-critical amounts of water (resins A to E of Table 3). The graphs are based on the data of Tables 1–3 appended.
Figure 2:
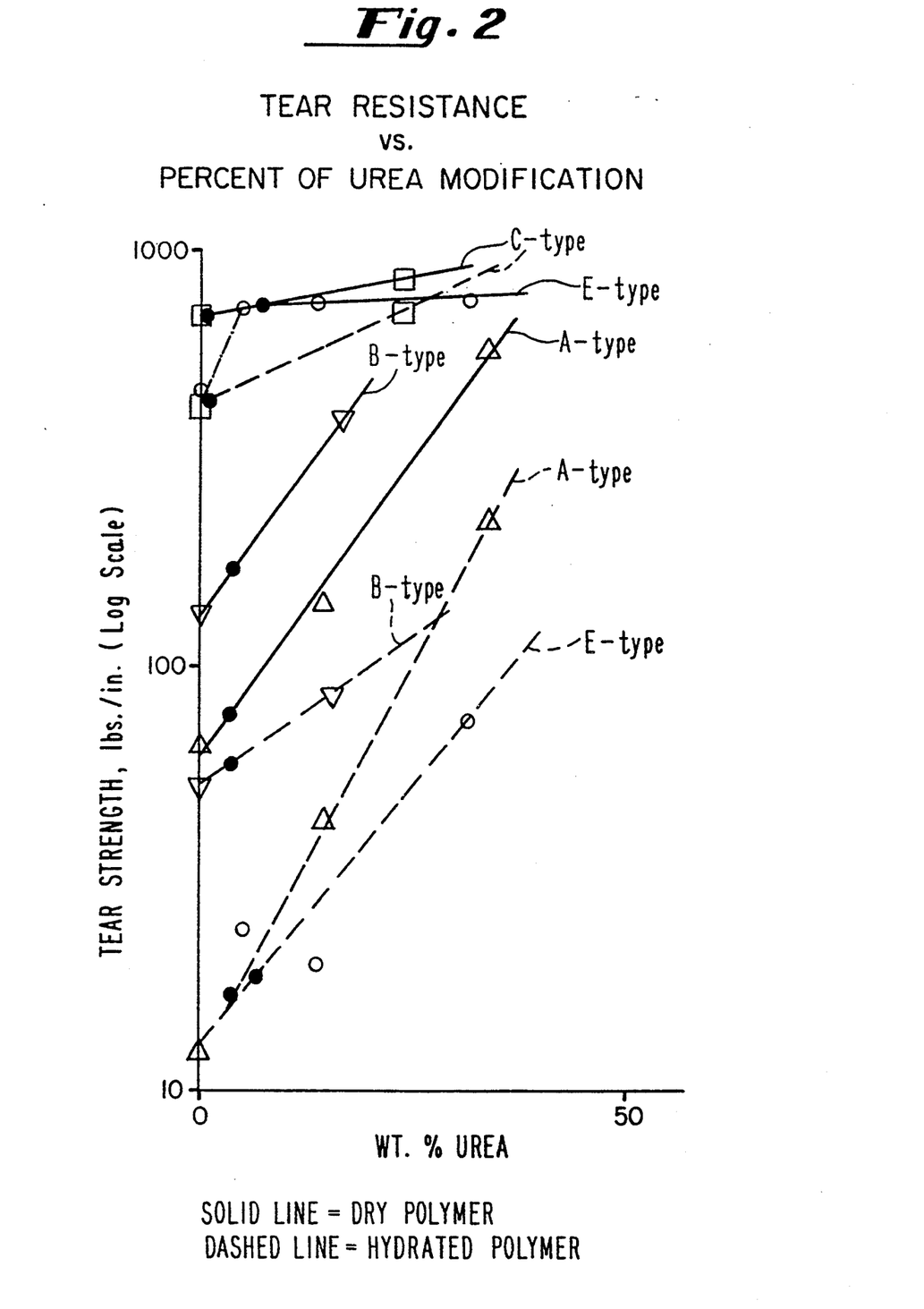
Figure 3:
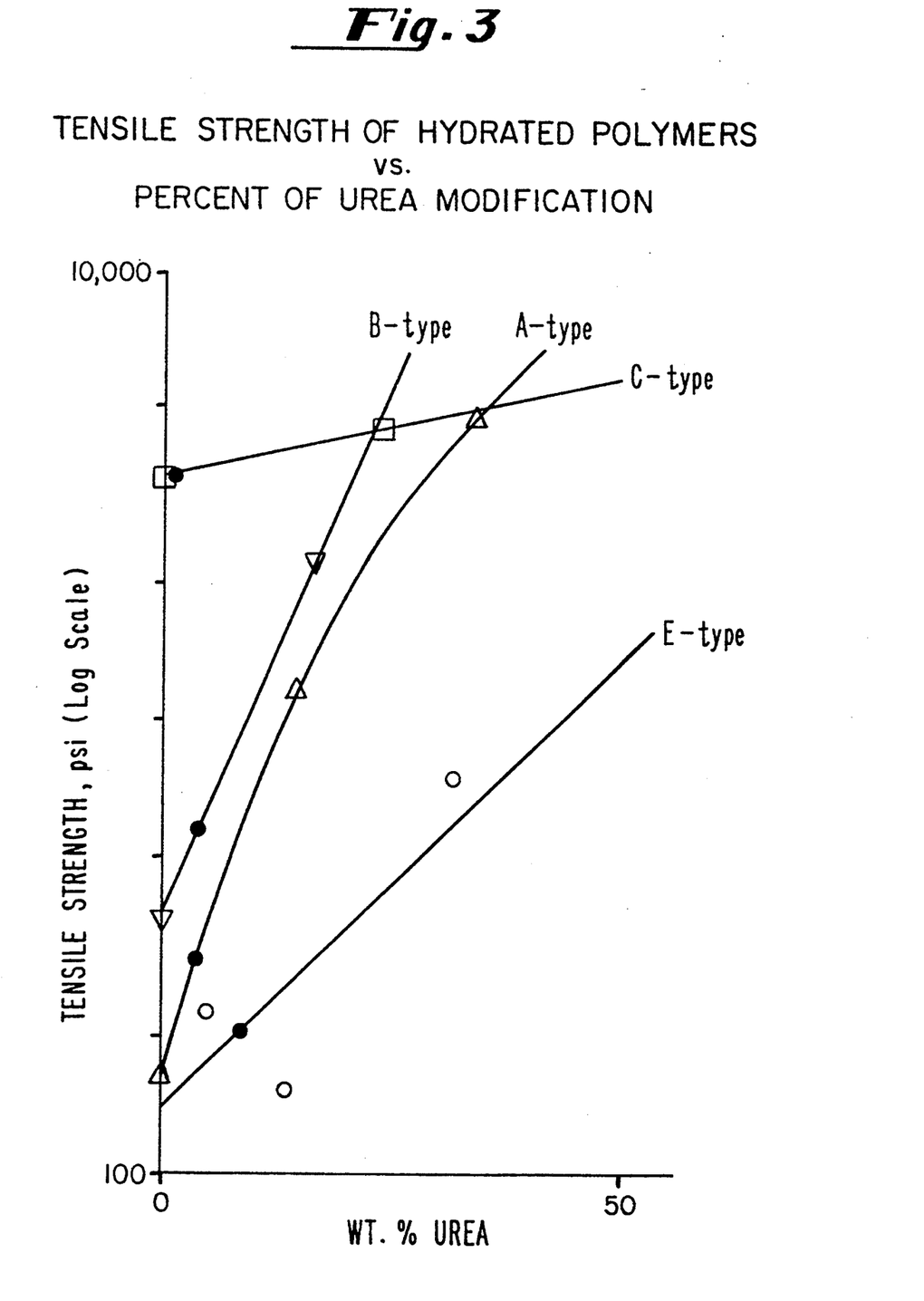
Figure 4:
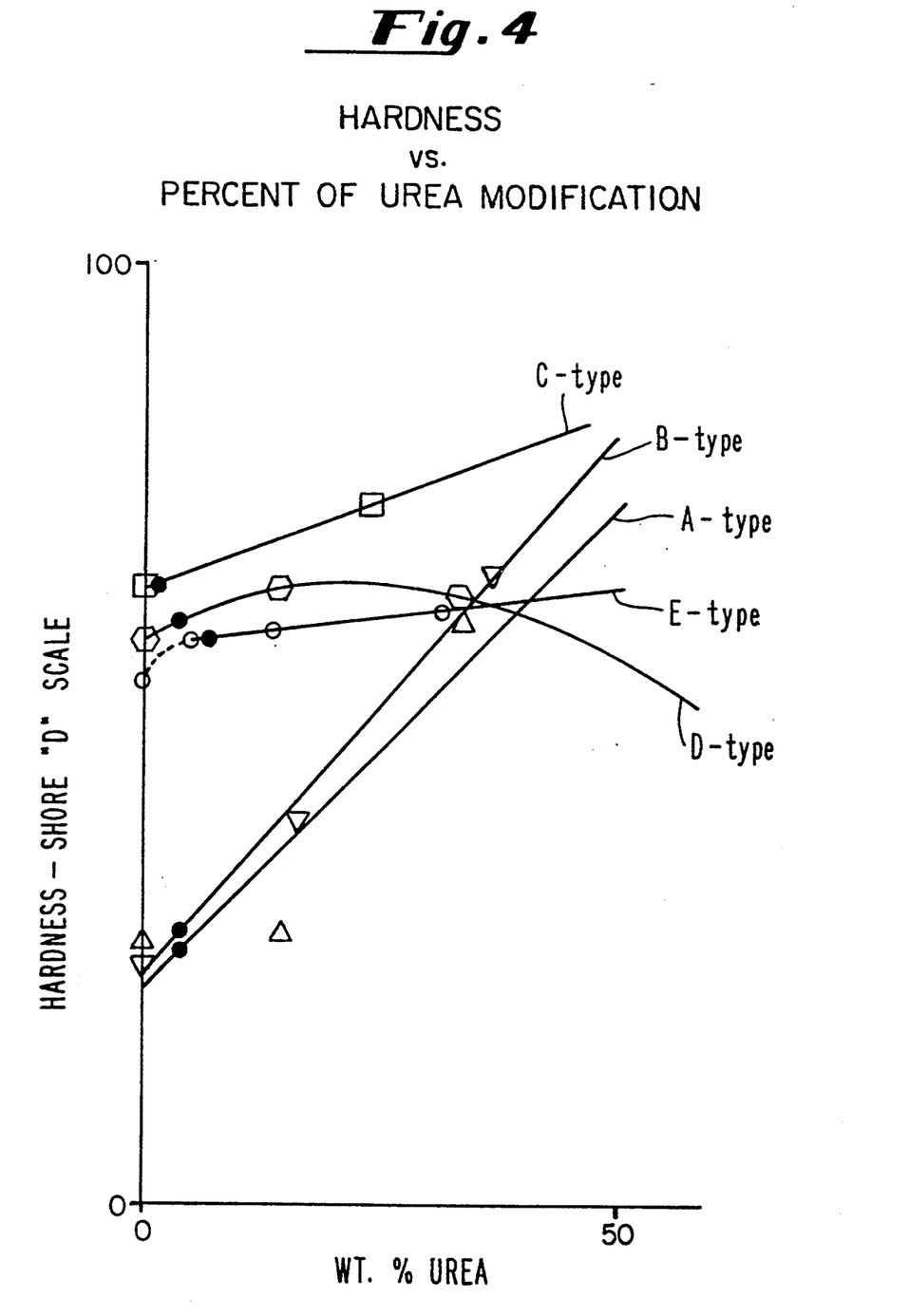
Figure 5:
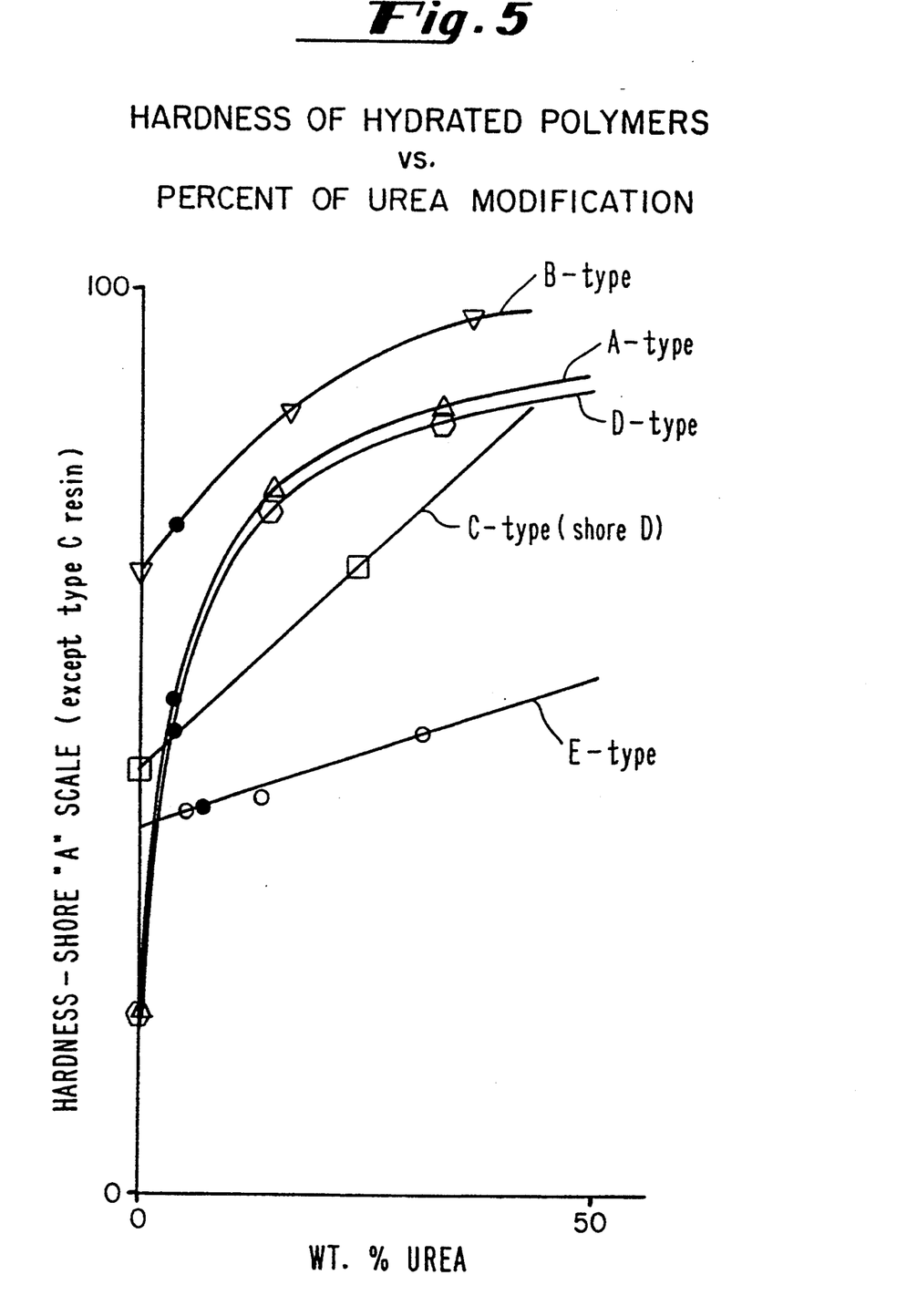
Figure 6:
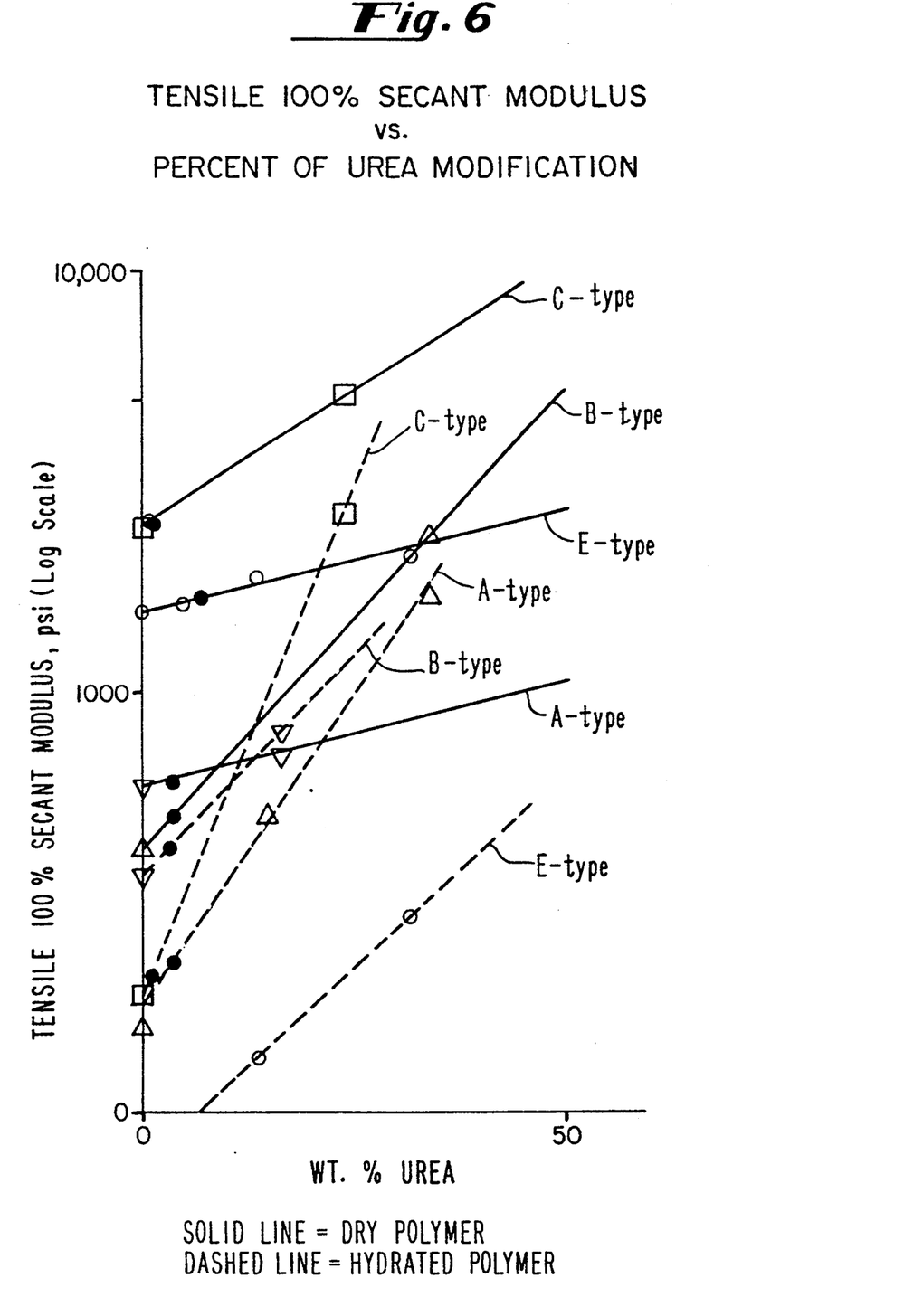

(3) Both the dry and fully hydrated resins show increased tensile strength when urea is present in the resin product; the increase in the strength is greatest for those resins which initially had the lowest values (see FIG. 3).

(4) The increased stiffness indicated by the modulus increase is evident by the "hand" (feel) of the resins. Those resins (wet or dry) which are initially soft (100% modulus below 600 psi at zero urea content) exhibit dramatic increases in modulus with increasing urea content (see FIG. 6). However, all of the resins with urea content show increases in tensile values at 100% elongation with increasing urea content.

(5) The fall-off of water absorbed with increase of urea content is evident (FIG. 1) but at the same time, as shown in FIGS. 2-6, tear resistance, tensile strength, hardness and secant modulus greatly improve in the case of resins of the invention as compared with the conventional hydrophobic polyurethanes A to E.

It is believed that the improved strength is due to urea segments in the resin being rather stiff with considerably less hydrophilicity than the normal components of hydrophilic polyurethanes. The urea segments impart strength, increase viscoelasticity, decrease water absorption and probably also increase the polarity, thus also shifting the spectrum of active agents, which can be carried by the resins and eluted or released at predetermined rates. Typical of the active agents are industrial substances, such as pH regulators, antioxidants, processing additives and reactants; drugs such as aspirin or other analgesic, or an antibiotic; agrichemicals including fertilizers, fungicides, insecticides, herbicides and pesticides of all types; topical agents such as deodorants, cosmetics and protective sun-screens; and a host of other substances such as hormones, depilatories, enzymes and other proteinaceous materials, and food additives such as flavors, fragrances, essences and spices.

The increased strength also renders the hydrophilic polyurethanes more suitable as shaped bodies (including cannulae and other tubular forms; contact and intraocular lenses; Seton strips for glaucoma treatment; corneal grafts; boluses for animals such as cattle and sheep; contraceptive devices such as IUDs; valves and body implants such as vascular grafts, esophageal or urethral prosthesis; mammery implants, reconstructive surgery implants, tendon sheaths and tissue extenders); as films (gloves, condoms, wound and burn dressings, membranes and denture liners); and as coatings (antidrag coatings for boats with and without antifouling agents; high-slip coatings for catheters and guide wires but also for industrial applications such as valves, pipes and other conduits, aeration equipment, etc.; anti-fog coatings; cosmetic coatings such as deodor ants, hairspray, sun-screens, depilatories, long-lasting perfumes, etc.).

TABLE 1

| | Hydrophilic Polyurethanes and Properties | | | | | | | |
|---|---|---|---|---|---|---|---|---|
| | A-Type Resins | | | | B-Type Resins | | | |
| Formulation[2]-Wt. % | $A_0$[6] | $A_1$ | $A_2$ | $A_3$[4] | $B_0$[6] | $B_1$ | $B_3$[5] | $B_4$[4] |
| Carbowax ® 1450[3] | 64.366 | 53.616 | 40.390 | 23.719 | 57.939 | 47.101 | 34.461 | 19.529 |
| Diethylene Glycol | 7.024 | 5.851 | 4.408 | 2.588 | 9.227 | 7.501 | 5.488 | 3.110 |
| Desmodur ® W | 28.609 | 39.456 | 52.801 | 69.621 | 32.834 | 44.192 | 57.438 | 73.085 |
| Water | 0 | 1.077 | 2.402 | 4.072 | 0 | 1.206 | 2.613 | 4.275 |
| [1]Catalyst $^{ml}/100$ g | 0.18 | 0.15 | 0.13 | | 0.15 | 0.15 | — | — |
| Wgt. % Urea | 0 | 14.61 | 33.71 | 59.74 | 0 | 16.42 | 36.87 | 63.06 |
| Hydration (% water content) | 63.2 | 49.7 | 31.8 | — | 0.58 | 46.9 | 18.9 | — |
| Expansion upon hydration (linear %) | 28.3 | 29.5 | 15.0 | — | 26.6 | 26.3 | 6.2 | — |
| Hardness (Shore A,D): | | | | | | | | |
| Dry | 27.3D, 75.8A | 28.2D, 78.4A | 61.4D | — | 25.2D, 85.2A | 41.0D | 67.0D | — |
| Wet | 20.0A | 77.4A | 96.4A | — | 68.2A | 86.3A | 97.0A | — |
| Tensile Strength (psi): | | | | | | | | |
| Dry | 246 | 3431 | 4740 | — | 529 | 5310 | — | — |
| Wet | 161 | 1150 | 4750 | — | 365 | 2280 | — | — |
| Tensile 100% Secant Modulus: | | | | | | | | |
| Dry (psi) | — | 423 | 2360 | — | 594 | 728 | — | — |
| Wet (psi) | 156 | 503 | 1680 | — | 364 | 800 | — | — |

TABLE 1-continued

| | Hydrophilic Polyurethanes and Properties | | | | | | | |
|---|---|---|---|---|---|---|---|---|
| | A-Type Resins | | | | B-Type Resins | | | |
| Formulation[2]-Wt. % | $A_0$[6] | $A_1$ | $A_2$ | $A_3$[4] | $B_0$[6] | $B_1$ | $B_3$[5] | $B_4$[4] |
| Tensile Elongation (%): | | | | | | | | |
| Dry | 2 | 488 | 288 | — | 187 | 575 | — | — |
| Wet | 110 | 273 | 208 | — | 111 | 375 | — | — |
| Tear Strength (lb/in): | | | | | | | | |
| Dry | 65 | 183 | 572 | — | 136 | 393 | — | — |
| Wet | 12 | 43 | 220 | — | 53 | 87 | — | — |

[1]Dibutyl tin dilaurate (T 9-Metal and Thermite Co., Rahway, New Jersey).
[2]NCO/OH = 0.98/1
[3]Polyoxyethylene glycol, No. Avg. Molecular Weight = 1450. Union Carbide Corporation
[4]Resin Products too brittle and powdery for measurement of physical properties. Outside scope of present invention.
[5]Other physical properties not measureable (outside scope of present invention).
[6]Outside scope of present invention.

TABLE 2

| | Hydrophilic Polyurethanes and Properties | | | | | | | |
|---|---|---|---|---|---|---|---|---|
| | C-Type Resins | | | | D-Type Resins | | | |
| Formulation[2]-Wt. % | $C_0$[5] | $C_1$ | $C_2$[4][5] | $C_3$[3][5] | $D_0$[5] | $D_1$ | $D_2$[4] | $D_3$[3][5] |
| Carbowax ® 8000 | — | — | — | — | 44.587 | 37.290 | 28.230 | 16.683 |
| Carbowax ® 1450 | 28.065 | 20.519 | 13.436 | 6.774 | 17.941 | 15.004 | 11.359 | 6.713 |
| Diethylene Glycol | 19.467 | 14.233 | 9.32 | 4.699 | 9.549 | 7.986 | 6.046 | 3.573 |
| Desmodur W | 52.468 | 63.513 | 68.882 | 83.635 | 27.923 | 38.665 | 51.999 | 68.996 |
| Water | 0 | 1.734 | 3.361 | 4.892 | 0 | 1.055 | 2.366 | 4.036 |
| [1]Catalyst ml/100 g | 0.13 | 0.10 | — | — | 0.20 | 0.15 | | |
| Wgt. % Urea | 0 | 23.92 | 48.37 | 73.40 | 0 | 14.31 | 33.17 | 59.15 |
| Hydration (% water content) | 24.7 | 12.1 | 2.9 | — | 80.7 | 51.0 | 38.1 | — |
| Expansion upon hydration (linear %) | 10.5 | 5.3 | 1.8 | — | 80.7 | 26.3 | 10.5 | — |
| Hardness (Shore A,D): | | | | | | | | |
| Dry | 65.2D | 74.0D | — | — | 59.6D | 65.1D | 64.4D | — |
| Wet | 46.6D | 68.8D | — | — | 19.8A | 76.0A | 85.0A | — |
| Tensile Strength (psi): | | | | | | | | |
| Dry | 3780 | 5510 | — | — | — | 4207 | — | — |
| Wet | 3430 | 4450 | — | — | 4.8 | 1000 | — | — |
| Tensile 100% Secant Modulus: | | | | | | | | |
| Dry (psi) | 2420 | 5190 | — | — | — | 2370 | — | — |
| Wet (psi) | 178 | 2680 | — | — | 56 | 869 | — | — |
| Tensile Elongation (%): | | | | | | | | |
| Dry | 360 | 140 | — | — | — | 398 | — | — |
| Wet | 463 | 296 | — | — | 78 | 132 | — | — |
| Tear Strength (lb/in): | | | | | | | | |
| Dry | 696 | 859 | — | — | — | 70.8 | — | — |
| Wet | 420 | 713 | — | — | 3.7 | 81 | — | — |

[1]Dibutyl tin dilaurate (T 9 - Metal and Thermite Co., Rahway, New Jersey USA).
[2]NCO/OH = 0.98/1
[3]Resin products too brittle and powdery for measurement of physical properties.
[4]Other physical properties not measurable.
[5]Outside scope of present invention.

TABLE 3

| | Hydrophilic Polyurethanes and Properties | | | | | | | | |
|---|---|---|---|---|---|---|---|---|---|
| | E-Type Resins | | | | Conventional Resins[5] | | | | |
| Formulation[3]-Wt. % | $E_0$[5] | $E_1$[5] | $E_2$ | $E_3$ | A | B | C | D | E |
| Carbowax ® 8000[4] | 88.613 | 83.405 | 74.787 | 57.780 | — | — | — | 42.3 | 81.8 |
| Carbowax ® 1450 | — | — | — | — | 61.4 | 55.5 | 27.5 | 17.0 | — |
| Diethylene Glycol | 2.479 | 2.333 | 2.092 | 1.616 | 6.7 | 8.8 | 19.1 | 9.1 | 2.3 |
| Desmodur ® W | 8.908 | 13.884 | 22.115 | 38.360 | 31.6 | 35.4 | 53.4 | 31.4 | 15.4 |
| Water | 0 | 0.377 | 1.006 | 2.444 | 0.3 | 0.3 | 0.1 | 0.3 | 0.5 |
| [1]Catalyst ml/100 g | 0.3 | 0.25 | 0.20[2] | 0.18 | 0.15[2] | 0.15[2] | 0.12[2] | 0.15[2] | 0.25 |
| Wgt. % Urea | 0 | 5.05 | 13.62 | 31.36 | 3.99 | 3.99 | 1.32 | 3.99 | 6.69 |
| Hydration (% water content) | gel | 85.4 | 78.4 | 63.5 | 66 | 60 | 30 | 60 | 80 |
| Expansion upon hydration (linear %) | gel | 97.3 | 67.4 | 38.9 | 50 | 39 | 12 | 38 | 73 |
| Hardness: | | | | | | | | | |
| Dry (Shore D) | 55.2 | 59.4 | 60.6 | 62.8 | | | | | |
| Wet (Shore A) | soft | 42.0 | 43.8 | 50.8 | | | | | |
| Tensile Strength (psi): | | | | | | | | | |
| Dry | 2200 | 6630 | 5100 | 5630 | 1700 | 1800 | 2970 | 900 | 575 |
| Wet | gel | 235 | 153 | 751 | | | | | |
| Tensile 100% Secant Modulus: | | | | | | | | | |

TABLE 3-continued

| Formulation[3]-Wt. % | Hydrophilic Polyurethanes and Properties | | | | | | | | |
|---|---|---|---|---|---|---|---|---|---|
| | E-Type Resins | | | | Conventional Resins[5] | | | | |
| | $E_0$[5] | $E_1$[5] | $E_2$ | $E_3$ | A | B | C | D | E |
| Dry (psi) | 1550 | 1610 | 1870 | 2130 | 180 | 437 | 1720 | 402 | 68 |
| Wet (psi) | — | 68 | 135 | 293 | | | | | |
| Tensile Elongation (%): | | | | | | | | | |
| Dry | 620 | 850 | 730 | 650 | 720 | 620 | 390 | 280 | 690 |
| Wet | — | 320 | 84 | 504 | | | | | |
| Tear Strength (lb/in): | | | | | | | | | |
| Dry | 464 | 737 | 758 | 760 | 65 | 97 | 374 | 58 | 52 |
| Wet | — | 24 | 20 | 62 | | | | | |

[1]Stannous Octoate (T 12 - Metal and Thermite Co., Rahway, New Jersey USA). All formulations except as indicated.
[2]Dibutyl tin dilaurate (T 9 - Metal and Thermite Co., Rahway, New Jersey USA).
[3]NCO/OH = 0.98/1
[4]Polyoxyethylene glycol, No. Avg. Molecular Weight = 8000. Union Carbide Corporation.
[5]Outside scope of present invention.

We claim:

1. A carrier system comprising an active agent the active agent is selected from a medicament, fungicide, pesticide, insecticide, fertilizer, fragrance, flavor, sunscreen, depilatory, cosmetic and a contraceptive and as a carrier vehicle therefor, a substantially non-covalently crosslinked hydrophilic substantially non-foaming polyurethane resin having improved tear strength and improved tensile strength and a urea content of from about 13.6 to 33.7 weight percent consisting essentially of the reaction product of a mixture of:

A. a diol component selected from at least one of
(1) a long chain poly(oxyethylene) glycol, having a molecular weight of from about 2500 to about 12,000
(2) a medium chain poly(oxyethylene) glycol or polyester glycol, having a molecular weight of from about 250 to about 2500,
B. at least one organic chain extender having a molecular weight of less than 250;
C. water; and
D. an organic diisocyanate;
wherein alternative mole ratios of the diol component A and water per mole of chain extender B are as follows:
(i) 0.4 to 0.5 of diol component (1), 1.5 to 10.0 of water;
(ii) 0.1 to 0.25 of diol component (2), 0.05 to 0.72 of water;
(iii) 0.25 to 0.50 of diol component (2), 0.25 to 1.00 of water;
(iv) 0.5 to 0.75 of diol component (2), 0.3 to 3.3 of water; or
(v) 0.06 to 0.07 of diol component (1), 0.1 to 0.2 of diol component (2) and 0.25 to 1.25 of water;
wherein the effective NCO:OH ratio is in the range of 0.85:1 to 1.1:1 and the amount of water in the reaction mixture is in the range of about 1 to about 2.5 wt. %.

2. A carrier system according to claim 1 wherein the hydrophilic polyurethane carrier vehicle is one wherein the diol component (A) comprises a long chain poly(oxyethylene) glycol having a number average molecular weight of about 5000 to 9000, and the chain extended (B) is diethylene glycol.

3. A carrier system according to claim 1 wherein the hydrophilic polyurethane carrier vehicle is one wherein the diol component (A) comprises a medium chain poly(oxyethylene) glycol and the claim extender (B) is diethylene glycol.

4. A carrier system according to claim 1 wherein the hydrophilic polyurethane carrier vehicle therefor is one wherein the diol component (A) comprises a mixture of a long chain poly(oxyethylene) glycol having a number average molecular weight of about 5000 to 9000 and a medium chain poly(oxyethylene) glycol, and the chain extender (B) is diethylene glycol.

5. A coating composition comprising substantially non-covalently crosslinked hydrophilic, substantially non-foaming polyurethane resin having improved tear strength and tensile strength and a urea content of from about 13.6 to 33.7 weight percent consisting essentially of the reaction product of a mixture of:

A. a diol component selected from at least one of
(1) a long chain poly(oxyethylene) glycol, having a molecular weight of from about 2500 to about 12,000
(2) a medium chain poly(oxyethylene) glycol or polyester glycol, having a molecular weight of from about 250 to about 2500,
B. at least one organic chain extender having a molecular weight of less than 250;
C. water; and
D. an organic diisocyanate;
wherein alternative mole ratios of the diol component A and water per mole of chain extender B are as follows:
(i) 0.4 to 0.5 of diol component (1), 1.5 to 10.0 of water;
(ii) 0.1 to 0.25 of diol component (2), 0.05 to 0.72 of water;
(iii) 0.25 to 0.50 of diol component (2), 0.25 to 1.00 of water;
(iv) 0.5 to 0.75 of diol component (2), 0.3 to 3.3 of water; or
(v) 0.06 to 0.07 of diol component (1), 0.1 to 0.2 of diol component (2) and 0.25 to 1.25 of water;
wherein the effective NCO:OH ratio is in the range of 0.85:1 to 1.1:1 and the amount of water in the reaction mixture is in the range of about 1 to about 2.5 wt. %, and an active agent selected from an antifogging agent, cosmetic, a hair spray formulation, a sun-screen and a perfume.

6. The carrier system of claim 2 wherein the agent is a medicament.

7. The carrier system of claim 2 wherein the active agent is a medicament.

8. The carrier system of claim 2 wherein the active agent is a medicament.

* * * * *